United States Patent [19]

Yap

[11] Patent Number: 5,001,150
[45] Date of Patent: Mar. 19, 1991

[54] NONDUSTY SPRAY DRIED MANCOZEB WATER-DISPERSIBLE GRANULES AND THE PROCESS FOR THEIR PRODUCTION

[75] Inventor: Warren H. Yap, New Castle, Del.

[73] Assignee: E. I. du Pont de Nemours and Company, Wilmington, Del.

[21] Appl. No.: 372,243

[22] Filed: Jun. 27, 1989

Related U.S. Application Data

[63] Continuation-in-part of Ser. No. 171,638, Mar. 22, 1988, abandoned.

[51] Int. Cl.$^5$ ............................................. A01N 47/10
[52] U.S. Cl. ..................................... 514/476; 514/951
[58] Field of Search ................................. 514/476, 951

[56] References Cited

U.S. PATENT DOCUMENTS

| | | | |
|---|---|---|---|
| 3,497,598 | 2/1970 | Luginbuhl | 514/476 |
| 3,657,446 | 4/1972 | Blackmore | 514/417 |
| 3,869,486 | 3/1975 | van den Boogaart et al. | 260/429 |
| 3,920,442 | 11/1978 | Albert et al. | 71/92 |
| 3,992,548 | 11/1976 | Pommer et al. | 514/476 |
| 4,066,760 | 1/1978 | Kawack et al. | 514/476 |
| 4,217,293 | 8/1980 | Adams, Jr. | 260/429 K |
| 4,394,316 | 7/1983 | Chao | 260/429 K |
| 4,593,040 | 6/1986 | Adam et al. | 514/395 |

FOREIGN PATENT DOCUMENTS

| | | |
|---|---|---|
| 273612 | 4/1964 | Australia . |
| 8100421 | 5/1984 | Czechoslovakia . |
| 1812574 | 6/1970 | Fed. Rep. of Germany . |
| 1642122 | 7/1970 | Fed. Rep. of Germany . |
| 2267039 | 12/1975 | France . |

Primary Examiner—Allen J. Robinson
Attorney, Agent, or Firm—Samuel S. Blisht

[57] ABSTRACT

Non-dusty water-dispersible mancozeb granules (90% > 100 micron diameter) are produced by a new process characterized by spray drying an aqueous slurry of ≧60% solids consisting of maneb or maneb dihydrate (5 microns, 50% 2-5 microns), a water soluble zinc salt and other formulation adjuvants.

5 Claims, 1 Drawing Sheet

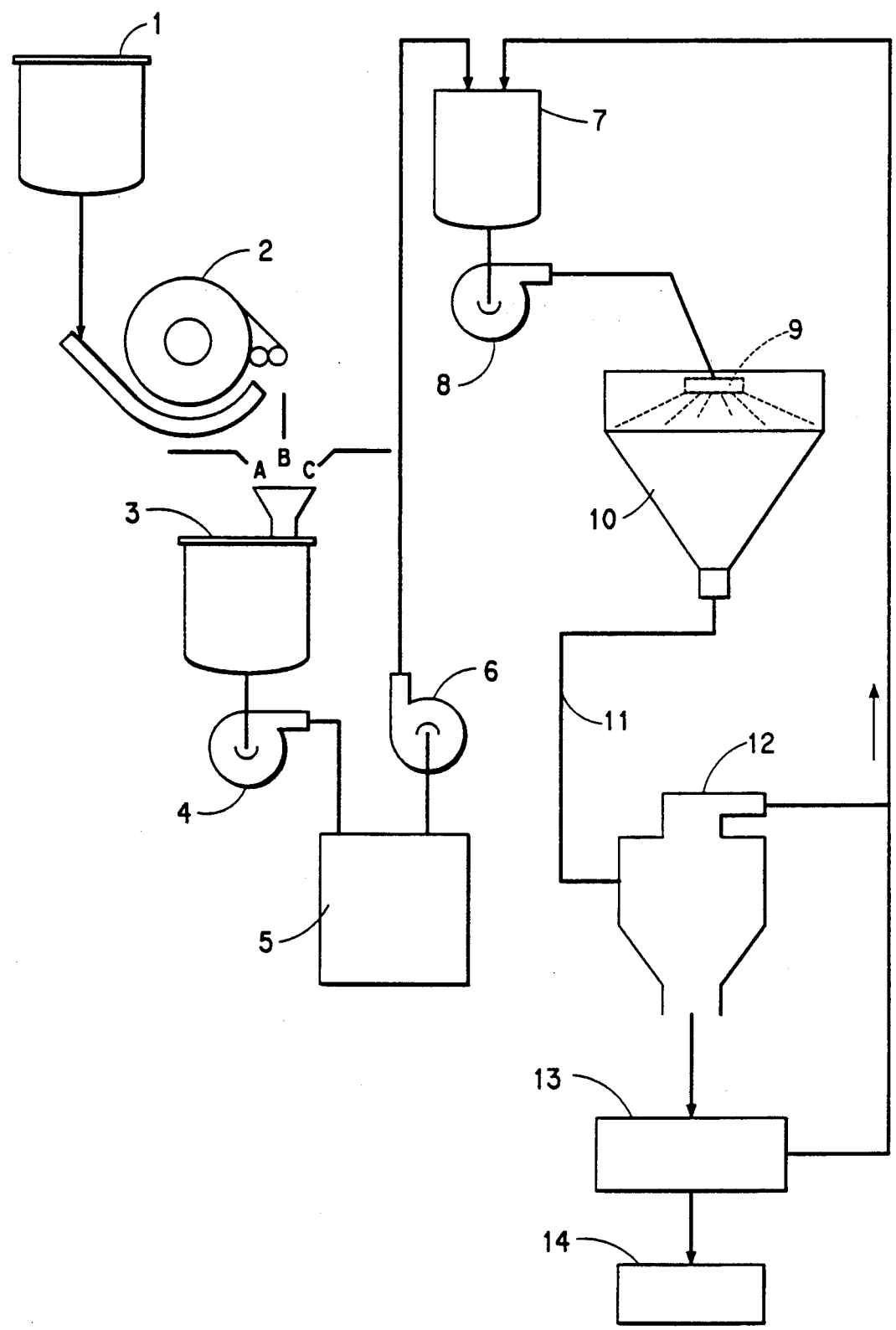

NONDUSTY SPRAY DRIED MANCOZEB WATER-DISPERSIBLE GRANULES AND THE PROCESS FOR THEIR PRODUCTION

CROSS REFERENCE TO RELATED APPLICATION

This application is a continuation-in-part of my co-pending application Ser. No. 07/171,638 filed on Mar. 22, 1988 now abandoned.

BACKGROUND OF THE INVENTION

This invention relates to methods for preparing nondusty water-dispersible granules containing mancozeb. Mancozeb, is presently recognized as the outstanding foliar fungicide for use on crops such as tomatoes but presents problems with dispersion in agricultural sprays. It has frequently been necessary to mix mancozeb with several different surface-active agents in order to obtain proper dispersion and also with stabilizers such as paraformaldehyde and hexamethylenetetramine.

It is customary in preparing mancozeb for use in agricultural sprays to react sodium or ammonium ethylene bisdithiocarbamate and manganese sulfate to form maneb which is then subsequently reacted with aqueous zinc salts. This crude mancozeb product is then prepared for drying by filtration or decantation to remove the sulfate salts such as manganese sulfate and then may be mixed with water. The mancozeb slurry is then pumped to an atomizer leading into a spray drier where water is removed from the mancozeb. Other pneumatic or dispersion driers in which the product in finely dispersed form is dried while being carried in a moving stream of heated gas are also used; for example, a Micro-Drier, Jet-O-Drier and the like.

Various surface-active agents, zinc ions, stabilizers such as paraformaldehyde and hexamethylenetetramine and other additives are then added to the mancozeb product in order to formulate the commercial mixture.

U.S. Pat. No. 3,497,598 incorporated herein by reference discloses an improvement over the art in that the solids concentration of the spray slurry could be increased to about 40% by the preaddition of goulac, a ligninsulfonate. The average particle size of the suspended maneb (or dihydrate) fed to the spray drier is taught to be approximately 15-20 microns.

However, the spray dried agglomerated product obtained is fine (90%<100 microns) and suffers from the disadvantages (including dustiness) during field use per U.S. Pat. No. 3,920,442 incorporated herein by reference; especially Column 2, lines 49-68 through Column 3, line 13.

SUMMARY OF THE INVENTION

Surprisingly, we have found that by using (1) mancozeb of smaller particle size (2.5-5 microns) premixed with formulation adjuvants in the spray slurry and (2) a total solids concentration of at least about 60% by weight in the spray slurry a larger spray dried granule results (90%>100 microns) which does not suffer from the disadvantages described by U.S. Pat. No. 3,920,442.

This invention comprises or consists essentially of spray-dried, nondusty, dry flowable granules of 105-840 micron diameter of mancozeb characterized by aging stability and low ethylene thiourea levels containing, by weight, about (a) 4-10% of a binding agent,
(b) 2-6% of a dispersant,
(c) 0.5-1.5% of paraformaldehyde,
(d) 5-7% zinc sulfate,
(e) 0.5-2% of a surfactant, and
(f) 73.5-88% of maneb.

This invention includes a process for the preparation of dry flowable mancozeb granules characterized by aging stability and low ethylene thiourea levels which comprises or consists essentially of spray-drying a milled aqueous slurry at least about 60% by weight of solids having the above composition.

A Preferred Composition of the invention consists of or consists essentially of
(a) 8% of binding agent,
(b) 4% of a sodium ligninsulfonate dispersant,
(c) 1% paraformaldehyde,
(d) 5.9% zinc sulfate,
(e) 1% of a sodium dialkyl naphthalene sulfonate surfactant, and
(f) 80.1% of maneb.

The preferred binding agent is sucrose, the preferred sodium ligninsulfonate dispersant is Marasperse® N-22, and the preferred sodium dialkyl naphthalene sulfonate surfactant is Morwet® IP.

BRIEF DESCRIPTION OF THE DRAWING

The accompanying drawing depicts an arrangement of unit operations to perform the process of this invention.

DETAILED DESCRIPTION OF THE INVENTION

The process is best described by referring to the drawing. The maneb slurry tank 1 contains a crude slurry of manganese ethylene bisdithio-carbamate, sodium sulfate, manganese sulfate, and other by-products of the reaction between sodium or ammonium ethylenebisthiocarbamate and manganese sulfate. This crude slurry is directed to filter 2 where the soluble sulfates and manganese sulfate are removed. The filter cake B is mixed with water, A, and a lignin sulfonate, C in repulp tank 3. Other additives such as the various surface active agents, zinc ions, stabilizers and other formulating agents are introduced here.

The filter cake B comprising maneb dihydrate particles of 15-20 microns along with the adjuvants are suspended as a 40-45% aqueous slurry in repulp tank 3.

The slurry is directed from repulp tank 3 to wet mill 5 via pump 4 where it is wet-milled (preferrably in a bead mill) to 2.5-5 micron particles. Dry solids (preferrably from recycle) and having essentially the same composition as the particles in the slurry from wet mill 5 are mixed with the slurry from wet mill 5 in mix feed tank 7 to obtain a concentration of equal to or greater than 60%.

The slurry concentration is obtained initially by the addition of dry-milled solids to the spray slurry, since such a highly concentrated slurry cannot be wet milled because of its viscosity. The concentrated slurry is conveniently sustained after start up by the addition of ground, dry recycle from the spray drying process.

Slurry from mix feed tank 7 is spray dried in 10, preferrably at an inlet temperature of 290°-320° C. and an outlet temperature of 122°-123° C.

The spray dried agglomerated product (granules) 11 is passed through cyclone separator 12 and then oscillating (SWECO) sieve 13 to recover a product of −20+140 U.S. mesh (90% >100 microns) which is packaged at 14.

Dry fines are recycled to mix feed tank 7.

Conversion in the spray drying process before sieving is typically 80–90% within the above particle size range (−20+140 U.S. mesh).

The granules by proper choice of adjuvants enjoy all the formulation advantages of the art including, e.g., increased maneb stability and low ethylene thiourea (ETU) levels upon aging and improved dispersibility.

The following examples are presented to illustrate but not restrict the present invention. Parts and percentages are by weight unless otherwise specified.

EXAMPLE 1

An aqueous maneb slurry, prepared by the addition of a 10% solution of manganese sulfate to a 90% aqueous solution of ammonium ethylenebisthiocarbamate is belt filtered to remove excess water and water soluble salts. The resulting wet cake is mixed with adjuvants (shown below) and water in a repulp tank to form a 40.1% aqueous solids concentration. The composition in the repulp tank is (dry basis) as follows:

|  | Percent |
| --- | --- |
| maneb (15–20 micron avg. dia.) | 80.1 |
| sucrose | 8.0 |
| Marasperse ® N-22 | 4.0 |
| Paraformaldehyde | 1.0 |
| ZnSO$_4$.H$_2$O | 5.9 |
| Morwet ® IP | 1.0 |

The slurry is pumped to a bead mill (wet mill) and milled to a particle size of 2.5–5 microns. The slurry is then pumped to a mix feed tank where premilled dry solids having the same composition and size as the solids in the slurry are added to obtain a solids concentration of 60.1%. This concentrated slurry is pumped at 1500 kg/hr. through a Niro rotary spray disc (Number F35, type AVOONPSS) in a spray drier, while maintaining the inlet air temperature at 295° C. and the outlet temperature at 122° C. The moisture content of the product under such conditions is less than 2%.

After fines (−140 U.S. mesh) build up upon passing through a cyclone separator and an oscillating (SWECO) sieve they are recycled to the mix feed tank as the dry solids to make up the concentrated slurry to 60.1%.

Dry mancozeb granules (−20+140 U.S. mesh) are collected at a rate of 721–811 kg/hr. at a drier conversion of 80–90%.

The following physical properties relating to the dispersibility of these mancozeb granules in water were determined before and after aging at 45° C. for 500 hrs.

|  | Before Aging | After Aging |
| --- | --- | --- |
| Dynamic Wet Time | 3 sec | 2 sec |
| Sedimentation |  |  |
| Long Tube (ml) | 0.05 | 0.05 |
| Spanish (%) | 23.0 | 26.6 |
| Foam @ 0.6% conc., cc | 900 | 700 |

In the determination of the dynamic wet time, the wetting time (seconds) of a 1 g sample of the formulation upon addition to 250 ml of water in a 400 ml beaker stirred at 850 rpm is measured.

The determination of sedimentation by the long tube method is disclosed in U.S. Pat. No. 3,920,442 (Column 9).

In the determination of sedimentation by the Spanish method, a 5 g sample of the formulation is dispersed in 500 ml of hard water (340 ppm salt content) in a 500 ml graduated cylinder. After 10 min, the bottom 10% of the mixture is separated and the weight of the solid in the thus separated mixture is measured. This result is reported as the percentage of the original sample weight.

In the evaluation of the foaming of an aqueous mixture of the composition, air is bubbled through 250 ml of a 0.6% mixture by weight in a 2 l graduated cylinder. After 10 min, the volume of the foam is measured.

The granulated formulation of the present invention after aging at 45° C. for 500 hrs and a control at room temperature (about 25° C.) were analyzed with the following results:

|  | Room Temperature | 45° C. |
| --- | --- | --- |
| mancozeb (%) | 76.41 | 76.97 |
| zinc (%) |  |  |
| total | 1.91 | 1.96 |
| free | 1.11 | 1.03 |
| ETU (ppm) | 90 | 90 |
| pH (5% aqueous) | 6.82 | 6.83 |
| Avg. Particle Size (after dispersion in water) (microns) | 2.33 | 2.20 |
| % >2.0 | 57.00 | 54.40 |
| % >5.0 | 22.80 | 20.30 |
| % >10 | 7.20 | 6.01 |
| formaldehyde (%) | 0.16 | 0.13 |

The % mancozeb was determined titrimetrically by titration of carbon disulfide formed by decomposition of the maneb.

The % zinc was determined by atomic absorption analysis. Total zinc refers to both uncombined and complexed zinc ions. Free zinc refers to the uncombined form only.

The amount of ethylene thiourea (ETU) was determined by liquid chromatographic analysis.

The pH of a 5% aqueous mixture was determined using a standard electrode.

The average particle size of dispersed solids was determined using a coulter counter.

The % formaldehyde was determined by gas chromatographic analysis.

What we claim is:

1. A process for preparing dry flowable non-dusty mancozeb granules consisting essentially of preparing an aqueous slurry of about 40–45% by weight of solids having in % by weight about
   (a) 4–10% of a binding agent,
   (b) 2–6% of a dispersant,
   (c) 0.5–1.5% of paraformaldehyde,
   (d) 5–7% zinc sulfate,
   (e) 0.5–2% of a surfactant, and
   (f) 73.5–88% of maneb, wet milling the thus obtained slurry to obtain particles in the range 2.5–5 microns, adding solids to the milled slurry having essentially the same composition and size as the solids in the milled slurry to obtain a second slurry having a solids concentration of at least about 60% by weight, spray drying the second slurry and thereafter recovering nondusty mancozeb granules (105-840 micron diameter) having improved aging stability and low ethylene thiourea levels.

2. The process of claim 1 wherein the solids consist essentially of in % by weight about
    (a) 8% of a binding agent,
    (b) 4% of a sodium ligninsulfonate dispersant,
    (c) 1% paraformaldehyde,
    (d) 5.9% zinc sulfate,
    (e) 1% of a sodium dialkyl naphthalene sulfonate surfactant, and
    (f) 80.1% of maneb.

3. The process of claim 2 wherein
    (a) the binding agent is sucrose,
    (b) sodium ligninsulfonate is the dispersant, and
    (c) sodium di-isopropyl naphthalene sulfonate is the surfactant.

4. The product of the process of claim 1.

5. A process for producing non-dusty water-dispersible granules of mancozeb, which consists essentially of spray-drying a slurry containing at least 60% solids, where the solid portion contains on a dry basis 4-10% of a binding agent, 2-6% of a dispersant, 0.6-1.5% of paraformaldehyde, 5-7% zinc sulfate, 0.5-2% of a surfactant, and 73.5-88% of maneb, where the particle size of the maneb is below 5 microns.

* * * * *